United States Patent [19]
Chauffard et al.

[11] Patent Number: 5,744,164
[45] Date of Patent: Apr. 28, 1998

[54] SUSTAINED RELEASE MICROPARTICULATE CAFFEINE FORMULATION

[75] Inventors: Francoise Chauffard, Vevey; Mark Y. A. Enslen, Yverdon; Pierre Tachon, Cugy, all of Switzerland

[73] Assignee: Nestec S.A., Vevey, Switzerland

[21] Appl. No.: 357,689

[22] Filed: Dec. 16, 1994

[51] Int. Cl.[6] .............................. A61K 9/16; A61K 9/54; A61K 9/58; A61K 9/60
[52] U.S. Cl. ........................ 424/496; 424/490; 424/497; 424/498; 424/462; 424/459; 514/952; 427/214; 427/2.19
[58] Field of Search ............................... 424/486, 485, 424/490, 496, 497, 471, 459, 461, 462

[56] References Cited

U.S. PATENT DOCUMENTS

| | | | |
|---|---|---|---|
| 3,835,221 | 9/1974 | Fulberth et al. | 424/20 |
| 4,001,480 | 1/1977 | Shank | 428/411 |
| 4,579,742 | 4/1986 | Lavie | 426/96 |
| 4,663,150 | 5/1987 | Panoz et al. | 424/494 |
| 4,708,874 | 11/1987 | De Haan et al. | 424/470 |
| 4,713,248 | 12/1987 | Kjornaes et al. | 424/468 |
| 4,716,041 | 12/1987 | Kjornaes et al. | 424/468 |
| 4,716,046 | 12/1987 | Lavie | 426/96 |
| 4,800,084 | 1/1989 | Zerbe | 424/458 |
| 4,820,521 | 4/1989 | Panoz et al. | 424/458 |
| 4,828,836 | 5/1989 | Elger et al. | 424/419 |
| 4,835,221 | 5/1989 | Bronstert et al. | 525/332.8 |
| 4,853,249 | 8/1989 | Takashima et al. | 427/3 |
| 4,971,785 | 11/1990 | Wilson et al. | 424/44 |
| 4,994,279 | 2/1991 | Aoki et al. | 424/494 |
| 5,026,709 | 6/1991 | Harwood et al. | 514/263 |
| 5,200,193 | 4/1993 | Radebaugh et al. | 424/468 |
| 5,202,128 | 4/1993 | Morella et al. | 424/469 |
| 5,330,766 | 7/1994 | Morella et al. | 424/490 |
| 5,378,474 | 1/1995 | Morella et al. | 424/469 |

FOREIGN PATENT DOCUMENTS

| | | |
|---|---|---|
| 0 377 518 | 1/1989 | European Pat. Off. . |
| 0 122 077 | 5/1990 | European Pat. Off. . |
| 0 222 411 | 8/1991 | European Pat. Off. . |
| 0 327 086 | 5/1992 | European Pat. Off. . |
| 71.07439 | 4/1971 | France . |
| 3 403 329 | 8/1985 | Germany . |
| 6-316517 | 11/1994 | Japan . |
| 929409 | 6/1963 | United Kingdom . |
| 931149 | 7/1963 | United Kingdom . |
| WO 85/03000 | 7/1985 | WIPO . |
| WO 87/06098 | 10/1987 | WIPO . |

OTHER PUBLICATIONS

Chemical Abstract, vol. 93, No. 20, 1980, Columbus, Ohio, US; abstract No. 191993; M. Dobrow et al. "Zero Order Drug Delivery From Double-Layered Porous Films: Release Rates From EC, HPC, and PEG Mixtures".

Br. J. clin. Pharmac. (1991), 32, 341-345, "A comparison of the central nervous system effects of caffeine and theophylline in elderly subjects", by G. Yu et al.

(List continued on next page.)

*Primary Examiner*—Edward J. Webman
*Attorney, Agent, or Firm*—Pennie & Edmonds

[57] ABSTRACT

The present invention relates to compositions and methods for increasing the alertness of an individual through the administration of a stimulant such as xanthine or an xanthine derivative and preferably caffeine. A particular composition has one or more layers containing the stimulant arranged about the cores of microparticles. This allows the composition to release a significant portion of the stimulant within about two hours after administration so that a level of alertness can be readily achieved. Thereafter, the balance of the composition is released within about 6 to 10 hours, so that the stimulant can provide alertness during that time, but then can dissipate to levels which would not affect the individual's ability to sleep. Also, the formulation is carefully designed so that the stimulant does not accumulate in the individual's system.

14 Claims, 5 Drawing Sheets

OTHER PUBLICATIONS

FCA-JUR/Pat/Cal No4755/00-RV; 108/94R; classe interne: 265, May 5, 1994, "Compte-Rendu De Recherche Documentaire"—subject *Cafiene a liberation prolongee*.

Pergamon Press Ltd., Great Britain 1992, Review Section, "An Update On Research With Coffee/Caffeine (1989–1990)", by B. Stavric.

Psychopharmacology (1990) 101:160–167, Original Investigations, "Benzodiazepines and caffeine: effect on daytime sleepiness, performance, and mood" by L.C. Johnson.

SUSTAINED RELEASE MICROPARTICULATE CAFFEINE FORMULATION

TECHNICAL FIELD

The present invention relates to a composition and method for administering a stimulant such as caffeine to a subject. More particularly, the composition is in the form of microparticles of the stimulant and a biodegradable matrix such that the stimulant is released from the composition over time.

BACKGROUND ART

It is well known that various stimulants can be administered to people to impart alertness and/or combat sleepiness. Typical stimulants which are used for these purposes include xanthine or xanthine derivatives of which caffeine is the most common example. Conveniently, caffeine is found in beverages such as coffee, tea and soda as well as certain foods such as chocolate and cocoa, so that an individual merely has to consume such foods or beverages in order to introduce caffeine into their system. One of the most common forms of administering caffeine is by consuming a cup of hot coffee early in the morning to help the individual to become more alert when beginning the day.

Ingesting large amounts of coffee or other caffeinated beverages is disadvantageous from the standpoint that the beverages must be continually consumed to provide the desired caffeine level in the individual's system so that an appropriate level of alertness can be achieved. Ingesting large amounts of such beverages requires a frequent trips to the beverage dispensing location to either prepare or obtain the desired amounts of such beverages, as well as frequent trips to the bathroom to eliminate liquids from the individual's body.

Another problem that often is encountered is that the individual who consumes significant amounts of caffeinated beverages late in the day may experience problems when attempting to go to sleep that evening. Whereas it is necessary to consume the caffeinated beverage to provide a sufficient level of alertness in the later-afternoon hours, this increased level is often retained in the body until late evening when the individual often attempts to go to sleep. These increased caffeine levels can thus interfere with the body's normal rest time.

What is needed therefore is a product or method for easily administering stimulants such as caffeine so that the individual can achieve the desired level of alertness during certain hours while avoiding the retention or buildup of caffeine in the individual's system to levels which will interfere with their normal sleep routines. The present invention provides one such solution to this problem.

SUMMARY OF THE INVENTION

The present invention relates to a method for increasing the alertness of a subject which comprises orally administering a single dose of a composition containing a stimulant of xanthine or a xanthine derivative to the subject, releasing at least about 20 to 50% by weight of the stimulant from the composition within about 2 hours after administration, and releasing the balance of the stimulant within about 8 to 10 hours after administration. Generally, a total of at least about 35 to 50% by weight of the stimulant is released from the composition within about 2 hours after administration and a total of at least about 70% by weight of the stimulant is released within about 5 hours after administration. Preferably, at least about 20 to 35% by weight of the stimulant is released from the composition within about 1 hour after administration, and a total of at least about 90% by weight of the stimulant is released from the composition within about 6 hours after administration.

Sufficient amounts of the stimulant are released from the composition into the subject to achieve a blood plasma level of at least about 4.5 µg/ml for the period of at least between about 2 and about 8 hours after administration of the composition, and preferably between about 2 and 4 hours after administration. The blood plasma level is generally increased above the base level of the subject by at least about 4.5 to 6 µg/ml within about 1 to 2 hours after administration. Since substantially all of the stimulant is released from the composition within about 8 to 10 hours after administration, the blood plasma level of the stimulant returns to the base level within about 24 hours after administration.

The invention also relates to a composition for the controlled release of the stimulant, the composition being in the form of microparticles which include a biodegradable matrix of at least one water-soluble material and the stimulant. The stimulant is generally in the form of solid microparticles which are substantially uniformly distributed throughout the matrix. Each microparticle is primarily in the form of a substantially spherical solid core of a pharmaceutically acceptable organic material with the matrix provided as a layer upon and surrounding a substantial portion of the outer surface of the core. Useful core materials include polysaccharides, sugar or sugar derivatives and optionally contain a diluent which is in intimate association with the core material.

The layer of matrix and stimulant surrounds substantially all of the core and can be present as the outermost layer of the microparticle. The matrix comprises a binding agent of a water-soluble material that binds to the stimulant and a release retarding agent of a water-insoluble material that retards the release of the stimulant from the composition. Advantageously, the water-soluble material is a synthetic polymer and the water-insoluble material is a shellac.

A coating substantially surrounding the layer of matrix and stimulant may be included to further delay the release of the stimulant from the matrix. The coating advantageously comprises a shellac applied at a thickness to further delay the release of the stimulant from the matrix and talc in an amount effective to help prevent the coated microparticles from sticking together. If desired, an additional layer of the matrix and stimulant may be provided upon and surrounding a substantial portion or substantially all of the coating to facilitate the initial release of the stimulant.

The amount of stimulant in the layers can vary, but for formulations which provide an initial release of the stimulant, the amount of stimulant in the inner layer will usually be greater than that of the outer layer. For example, the amount of stimulant in the inner layer can be between about 55 and 95% of the total amount while the amount of stimulant in the outer layer is between about 5 and 45%. In order to obtain the preferred stimulant release rates described herein, the inner layer should contain at least about 80% of the amount of stimulant.

The composition may be in the form of a capsule which contains a plurality of microparticles having a final diameter of between about 0.7 and 1.2 mm with the amount of stimulant in each capsule being between about 100 and 700 mg, and preferably between 200 and 400 mg. The most advantageous stimulant is caffeine, and the desired dose is conveniently administered orally in one or two capsules.

The invention also relates to a method for making these compositions by dispersing a stimulant in the form of a plurality of solid particles into a biodegradable matrix. A plurality of neutral microparticles having substantially spherical solid cores of a pharmaceutically acceptable organic material may be provided with a layer of the matrix and stimulant applied upon and around a portion of the outer surfaces of a majority of the cores to form active microparticles for delivering the stimulant. Also, the matrix can be made by preparing a matrix forming mixture of particles of the stimulant, a binding agent of a water-soluble material that binds to the stimulant and a release retarding agent of a water-insoluble material that retards the release of the stimulant, and spraying the matrix forming mixture upon the cores to deposit the layer of matrix thereon.

Advantageously, the cores have an initial diameter of about 350 and 1000 µm, and preferably about 500 to 630 µm, while the stimulant is in the form of a powder having a particle size of less than about 100 µm. The humidity of the air around the particles during the spraying step is advantageously controlled to below about 10% and preferably to about 2% or less. When a binding agent of polyvinyl pyrrolidone and a release retarding agent of shellac are used, the matrix forming mixture is simply achieved by combining the stimulant particles with the polyvinyl pyrrolidone, shellac and a liquid vehicle, such as ethanol.

Also, a coating can be provided upon and substantially surrounding the layer to further control the release of the stimulant from the matrix. When used, the coating comprises shellac to delay the release of the stimulant from the matrix and talc in an amount effective to help prevent the coated microparticles from sticking together.

If desired, a second layer of the matrix forming mixture may be applied upon and substantially surrounding the coating as an outer layer of the microparticles. This second layer can be applied by spraying additional amounts of the matrix forming mixture described above upon the coated cores.

DETAILED DESCRIPTION OF THE INVENTION

In accordance with the most preferred embodiment of the invention, there is provided a sustained release caffeine formulation which can be administered to an individual at one time to provide an increased level of alertness for a period of about 1 to 10 hours after administration. This level is achieved by raising the individual's blood plasma caffeine levels to values which provide such alertness during those time periods. Afterwards, the individual's blood plasma levels of caffeine will diminish back to the baseline level thus avoiding interference with the individuals engagement of sleep activity.

Conveniently, the formulations of the invention are intended to be consumed in the morning, such as after the individual awakens from the prior night's sleep. For example, the formulation may be consumed with the breakfast meal so that the caffeine levels of the individual will be raised to alertness levels within the following hour or two. This increased alertness level can coincide with the individual's arrival at work, with the increased level being retained for the entire 8 hours of the individual's work day. As the individual returns home from work, the caffeine levels begin to diminish below the stimulation level such that by bedtime the individual would be able to go to sleep without being affected by elevated levels of caffeine in his or her body. Moreover, by the following morning, the stimulant level will have returned to the individual's baseline level, thus allowing the process to be repeated without building up levels of stimulant in the individual's system.

The present formulations can be administered alone but can be consumed along with additional stimulants such as those found in caffeinated beverages. Furthermore, depending upon the amount of caffeine which is ingested by an individual through the consumption of such beverages or caffeinated foods, the amount of active ingredients in each formulation can be varied. Accordingly, a person who consumes large amounts of caffeinated foods or beverages may require only a smaller dosage of the active ingredient, whereas a person who consumes very little caffeinated foods or beverages might require a larger dosage of the active ingredient to achieve the same level of stimulation or alertness level.

In order to achieve the alertness level of approximately 4.5 µg/ml in the individual's blood plasma, it has been found that formulations containing between about 100 and 700 mg of caffeine are suitable. For convenience, a typical capsule is formulated to contain approximately 300 mg of caffeine so that the either one or two capsules can be administered to the individual to achieve the desired alertness level depending upon the amount of caffeine that is concurrently consumed such as when drinking caffeinated beverages.

Caffeine, which is a xanthine based stimulant (i.e., 1,3, 7-trimethyl xanthine), is typically used for its psychomotor stimulant action. The "alertness" or "awakening" effect of this compound depends upon its plasma level in the user's body. Caffeine is rapidly absorbed by the oral route, where its stimulating affect is rapid but transitory. For example, the oral administration of 350 mg of caffeine in aqueous solution yields a maximum plasma level of approximately 8.3 µg/ml for about 47 minutes when administered to healthy, caffeine-fasting volunteers.

The purpose of using a slow or sustained release galenic formulation is to maintain the plasma levels of caffeine which will cause a stimulating effect about 1 to 2 hours after administration and for about 4 to 8 hours thereafter. For example, the formulation can be taken with breakfast with the plasma concentration gradually increasing slowly and steadily to obtain its stimulating effect without causing undesirable cardiovascular reactions. The stimulating effect is generally achieved within about 1 to 2 hours, when the stimulation threshold is achieved. This level can vary depending upon the baseline blood plasma level of the individual, which in turn depends upon metabolic rate and weight of the individual, the amount of caffeinated foods or beverages consumed, the amount of sleep or rest achieved during the previous night, etc.

When the appropriate dosage is administered by way of the present sustained release formulations, the caffeine plasma level can be raised to remain above the stimulant threshold to thus significantly enhance alertness for a period of at least about 2 to 6 hours and preferably about 2 to 10 hours after administration. This would diminish the effects of post-prandial hypotension including the urge to take a nap in the afternoon. Thus, the alertness level of the individual can be maintained until late afternoon or early evening.

At about 8 to 10 hours after administration, the plasma level of caffeine in the individual would begin to drop below the stimulant threshold. This reduction would of course increase over time and would be sufficiently low at the individual's bedtime to ensure a normal nights sleep. The plasma levels continue to drop until approximately 24 hours after administration where the residual plasma level due to the administration of the formulation would be close to zero. This prevents a cumulative daily effect or buildup of the stimulant which ultimately might cause insomnia.

The present invention is useful with a wide variety of stimulants. It is preferred, however, that the stimulant be xanthine or a xanthine derivative, of which the most well know is caffeine. The mechanisms of action of caffeine have been studied widely both from the standpoint of its stimulant action on the central nervous system and with regard to pharmacological effects. Similar effects can be obtained with xanthine or other xanthine derivatives such as aminophylline, dyphylline, oxtriphylline, theobromine, and theophylline.

Caffeine from natural foods can be found in coffee, tea, cola and other soft drinks, cocoa and chocolate. Conventional over the counter caffeine tablets contain between about 100 and 250 mg of anhydrous caffeine and can be taken every 3 to 4 hours to maintain the desired level of alertness. Although caffeine is rapidly absorbed when administered orally, its effect is transitory, thus requiring periodic administration for continued stimulation.

With regard to toxicology, the maximum tolerated dose of the sustained release caffeine formulation of the invention in the dog, when administered orally on a daily basis, with the dose of caffeine increased every three days until the onset of signs of toxicity, is approximately 80 mg. Thus, a person weighing 70 kg should be able to consume as much as 5600 mg per day without any adverse effects.

The preferred process for manufacturing the present formulations will now be described. All production steps are conducted in clean rooms and with appropriately cleaned equipment in accordance with the good manufacturing practices of the pharmaceutical industry. The rooms used for each production phase are independent and isolated from other pharmaceutical operations in order to prevent contamination.

The present formulations are made by first obtaining nontoxic organic materials in the form of microparticles. While any edible nontoxic organic material can be used, it is preferred to select a polysaccharide, sugar or a sugar derivative since these are well established as acceptable materials which have little if no side effects when consumed. Although sucrose is preferred, other polysaccharides, sugars or sugar derivatives, either alone or in combination with diluents such as starch or grain based fillers can be used.

The most preferred materials are neutral microparticles containing 75% sucrose, 24.9% corn starch and 0.1% stearic acid, in the form of small spheres having a diameter of between 500 and 630 microns. The composition and size of these neutral microparticles are not critical, and the preferred materials were selected due to their commercial availability from a variety of sources. Alternatively, neutral microparticles can be manufactured according to conventional techniques using the ingredients mentioned above and a small amount of a production solvent such as demineralized water. Advantageously, the final microparticles would contain a moisture content of 2% or less.

Neutral microparticles may be prepared as follows. In a stainless steel flat bottom turbine device having a capacity of 400 kg, 70 kg of sucrose are added and then heated until a temperature of 60° C. is reached. In a separate 600 kg stainless steel tank, 107 kg of sucrose and 50 kg of water are mixed and heated to 85° C. to form a syrup. The syrup is sprayed at 60° C. in a conventional manner onto the heated sucrose particles in the turbine to provide a sticky surface on the surfaces of the microparticles. A dusting step using corn starch is conducted after each spraying step to sufficiently reduce the stickiness of the particle surfaces to prevent or at least minimize agglomeration of the microparticles. The syrup spraying and corn starch dusting steps are repeated until the entire syrup is applied to the sucrose particles. Thereafter, a mixture of 120 g stearic acid and 2 kg of ethyl alcohol is prepared, heated to 95° C. and then added to the turbine. This is done to facilitate handling of the microparticles, as the stearic acid acts as a lubricant to assist in the movement of the microparticles through subsequent processing steps. The final products are dried and sieved to obtain neutral microparticles having diameters of 500 to 630 microns.

These microparticles are coated with a matrix material that includes particles of the stimulant and a binding agent which adheres the stimulant particles to the neutral microparticles. When caffeine is selected as the stimulant, it is preferred to utilize particles of approximately 100 microns or less, with at least 90% of the microparticles having an average diameter of over 75 microns and no more than about 20% of the microparticles being less than 50 microns. The preferred caffeine powder is a caffeine base.

The binding agent is a water-soluble material that binds the stimulant to the microparticles. Advantageously, the water-soluble material is a synthetic polymer which is hydrophilic. Polyvinyl pyrrolidone is the most preferred polymer because it is a pharmaceutically acceptable material. One commercial form of this material is POLYVIDONE which is available from BASF. Other polyvinyl pyrrolidones or similar water soluble organic polymers such as polyacrylate esters can be used provided that such polymers are non-toxic and capable of binding the stimulant particles to the microparticles.

To obtain a sustained release composition, a release retarding agent may be included in the matrix. Preferably, the release retarding agent is a water-insoluble material that retards the release of the stimulant from the composition. One suitable water-insoluble material is a shellac. The preferred shellac utilized in this invention is a white lacquer derived from bees wax and is a conventional commercial product. Other components such as synthetic waxes can be used provided that they are non-toxic and sufficiently hydrophobic to delay the release of the stimulant from the composition.

The binding agent and release retarding agent may be combined in a suitable solvent carrier before being applied to the microparticles. The carrier should be a suitable non-toxic pharmaceutically acceptable compound into which each agent is soluble and which is sufficiently volatile to be removed from the formulation after depositing the agents. The most preferred solvent is ethanol, a pharmaceutically acceptable liquid, although other solvents such as methanol can be used, if desired.

The relative amounts of the binding agent and release retarding agent in the matrix are selected to achieve the desired adhesion and release of the stimulant. When a single matrix layer is applied, greater amounts of release retarding agent should be included, whereas for a more rapid release, greater amounts of the binding agent are used. Generally, between about 20 and 80 weight percent of each agent may be included in the solvent and resulting matrix, with between about 40 and 60 weight percent and preferably substantially equivalent amounts of each being used for convenience when other layers or coatings are to be included.

To apply the matrix, 25 kg of neutral microparticles of the desired size are placed into a coating turbine of the type made by HYDROTHERMICA. This turbine is a stainless steel tank having a truncated cone shaped opening. The diameter of the tank is 125 cm and the useful capacity of the tank is about 400 liters, although the total volume is 735 liters. The turbine rotation speed can vary from about 3.5 to 15.5 RPM.

In a separate stainless steel tank, a solution of equal parts of 31.7 kg of a 20% solids PVP ethanol solution and 31.7 kg of a 40% solids dewaxed white shellac ethanol solution are combined and heated to 95° C. The neutral microparticles are rotated at approximately 15.5 RPM in the turbine while the solution of PVP and shellac is sprayed into the turbine using an air gun (GRACCO MONARK type or equivalent).

After each spraying of approximately 1 kg of the solution, the caffeine in powered form is applied by sprinkling onto the microparticles as they are rotated in the turbine. Approximately 2.4 kg of caffeine powder is applied for each 1 kg of solution. The spraying and sprinkling steps are repeated until the entire amount of the active ingredient has been applied to the microparticles. This provides a layer of matrix which surrounds substantially all of the outer surface of the microparticles. Although, it is not entirely necessary, the layer should complete surround the surface.

Although the spraying and sprinkling steps are alternated and repeated several times to intimately mix the stimulant with the PVP and shellac, it is also possible to apply all amounts of these components at one time. In some cases, this may result in the incomplete surrounding of the neutral microparticles with the matrix. It is desirable for a substantial portion, such as at least about 75%, of the outer surface area of the microparticles to be covered by the matrix, for the preferred formulations.

Any small clumps of the matrix containing microparticles can be removed by screening through the stainless steel sieve mentioned above. The caffeine containing microparticles are then dried by the use of infrared lamps which are mounted in the body of the turbine while the turbine is rotated at about 3.5 RPM for about 12–18 hours. To ensure completion of the drying process, the microparticles may be placed in a forced air oven (ARPIN type or equivalent) at approximately 40° C. for an additional 24 to 48 hours. When the moisture content of the microparticles reaches 2%, the microparticles are then considered to be dry and are collected for further processing.

During the application of the matrix, it is important that the humidity in the area where the material is being applied be controlled to a relatively low level. A humidity of less than about 10% and preferably 2% or less should be used for optimum manufacture of the composition. The low humidity conditions can be easily achieved by conducting the process in a closed reactor and maintaining the environment around the microparticles at the desired moisture level.

The next step is the application of a coating of a water-insoluble material to further delay the release of caffeine from the formulation. A solution of 40% shellac in ethanol is prepared and is sprayed onto the activated microparticles as they are rotated in the turbine at about 15 RPM. After the shellac solution is sprayed onto the activated microparticles, talc is dusted over the particles. The talc allows the tackiness of the product to be reduced so that they will not stick together during further processing. Talc also stabilizes the shellac in the coating and also makes drying of the coated microparticles easier. It is believed that talc closes the pores of the polymer network to also increase the retarding effect on the release of the stimulant. Conventional talc power (pharmaceutical grade) is used although other non-toxic inorganic powder materials such as zinc oxide, silica, or alumina are suitable. After the coating layer has been applied the product is then dried by operating the turbine at about 3.5 RPM for about 14–16 hours.

Finally, an outer layer of matrix is applied over the coating. As noted above, this layer includes the same components as the inner layer and is applied in the same manner. The amount of stimulant applied in the outer layer is generally less than that which is applied in the inner layer and is generally used to provide an initial release of caffeine from the formulation. This layer may be considered optional from the standpoint that when a highly delayed release of caffeine is desired, the coating is sufficient to delay the release of caffeine from the formulation. For example, an individual who is accustomed to consuming caffeinated beverages such as coffee in the morning and who does not feel the need for an additional stimulant can take capsules made of microparticles which include the outer coating to delay the release of the stimulant from the composition until later in the day, such as the afternoon. Later in the day, the stimulant will be released from the composition to compensate for the wearing off of the initial stimulation obtained through consumption of the coffee.

It is useful to include the outer layer to provide an initial release of the stimulant. The outer layer allows the formulation to release the stimulant rapidly, so that the stimulant threshold is achieved between about 1 and 2 hours, with the sustained release of the stimulant occurring over the following 6 to 8 hours.

The spraying procedures are conducted so that essentially all of the microparticles are provided with the matrix layers and coating. In particular, it has been observed that the layers and coating are applied substantially completely around the neutral microparticles which are of substantially spherical shape. Thus, the final active microparticles are also spherical.

After the desired structure of the microparticles has been prepared, the active microparticles can be formulated for administration. The preferred administration route is oral, and the microparticles are encapsulated in conventional pharmaceutical capsules. Size No. 1 two part capsules have been found to be eminently suitable, although other capsule sizes and configurations can be used, if desired. The caffeine containing microparticles must have a size that is equal to or less than 1.18 mm so that the appropriate number of microparticles are placed in the capsule to obtain the desired amount of caffeine. These capsules are filled using conventional encapsulation machines.

Each step in the process is controlled so that the appropriate quantity of caffeine in each batch of material is within the desired parameters. Appropriate quality control tests are conducted to assure that the desired amount of stimulant is included in the active microparticles. When manufacturing capsules, the amount of microparticles placed into the volume of the capsule determines the overall amount of stimulant that will be provided in the capsule. These monitoring and capsule filling techniques are conventional in the pharmaceutical industry.

After the capsules are filled, a determination of titer and weight can be performed in order to confirm that the production yield is within specifications. For example, if a 300 mg formulation is desired, the variation in each tested capsule should not be more than about ±5% (i.e., between 285 and 315 mg). In a test sample of 20 representative capsules, no more than two can vary by more than 7.5% and none can deviate by 15% in order to be within product specifications.

Figure 1:
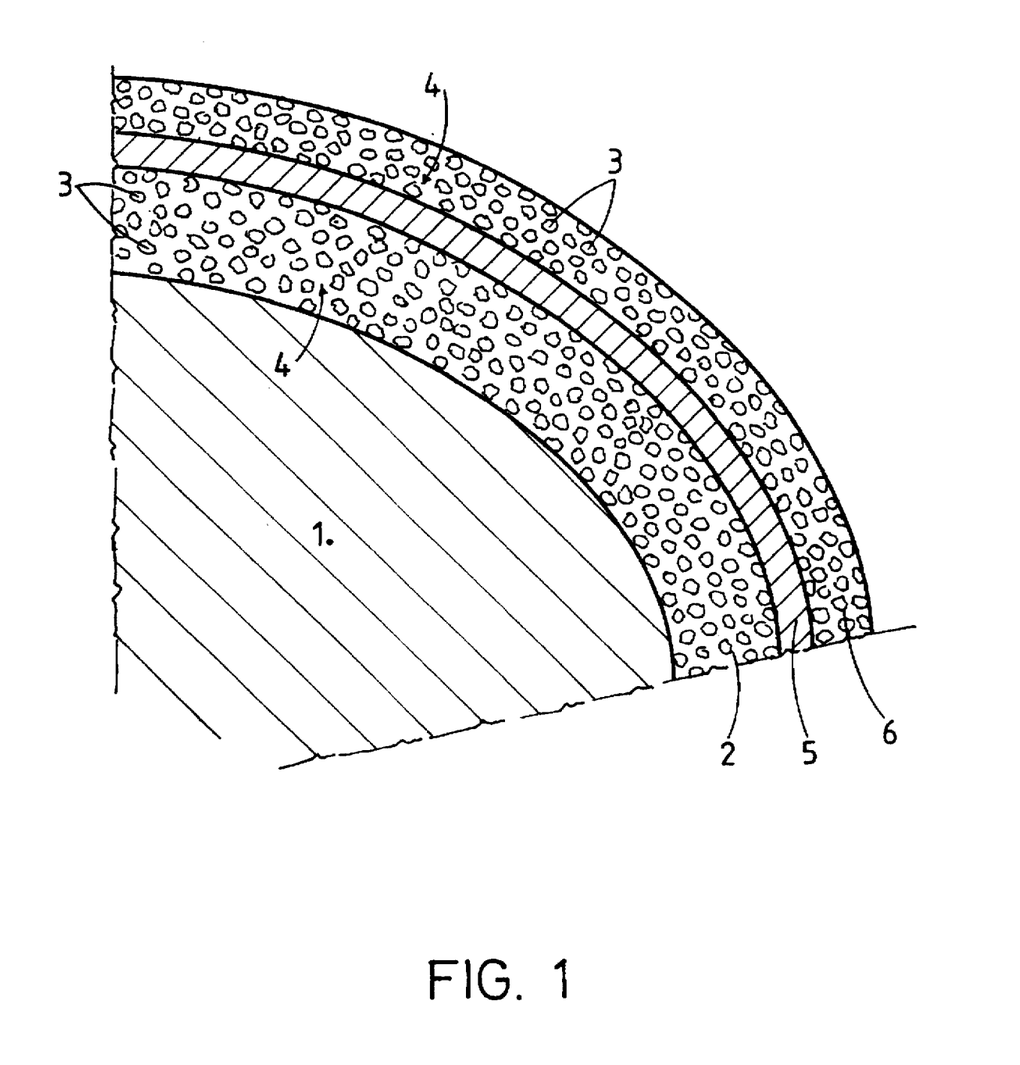
FIG. 1 is an exploded cross-sectional view of a portion of the sustained release microparticles of the invention.

FIG. 1 is an exploded cross-sectional view which illustrates a preferred active microparticle according to the invention. This microparticle includes a core 1 composed of the sucrose, corn starch, stearic acid mixture described above, inner 2 and outer 6 layers of matrix and an intermediate coating 5. The inner layer 2 illustrates the caffeine particles 3 and the binder material of PVP and shellac 4. This layer 2 preferably includes between about 85 and 90% of the amount of caffeine which is intended to be included in the formulation.

Layer 5 represents the shellac and talc coating which acts as a barrier to reduce the release of caffeine from inner layer 2.

The outer layer 6 is similar in composition to inner layer 2 except that it is applied at a lesser thickness than the inner layer, and preferably contains 10 to 15% of the overall amount of the stimulant in the formulation.

As shown by the examples, this particular formulation is capable of releasing 20–35% of the caffeine in about 1 hour, 35–50% in about 2 hours, a total of 70–90% in about 5 hours and greater than 90% in about 6 hours. Also, the plasma levels of caffeine in-the individual to which the formulation is administered can be increased to 4.5 µg/ml up to as high as 10 µg/ml, depending upon the dosage of caffeine in the formulation. Moreover, after about 10 hours the plasma levels will be reduced sufficiently so that the stimulant will not be effective whereas at the end of approximately 24 hours the plasma levels will return to the individual's base level.

The amount of caffeine administered to the individual as measured by blood plasma levels can vary during the release of the caffeine from the composition and is intended to achieve certain levels at certain time periods after administration. For individuals who obtain a good nights sleep or who are not sleep deprived, a level of approximately 6 to 6.3 µg/ml is necessary to achieve the desired stimulation and alertness properties. "Non-sleep deprived" is intended to mean a person who obtained at least 6 and between about 7 and 9 hours of sleep during the preceding night. Due to the achievement of an appropriate rest period, it has been found that at relatively higher levels of plasma caffeine must be achieved in order to provide the desired stimulation and alertness during the day. In particular, the 6.3 µg/ml level can easily be achieved within about 1 to 2 hours after administration of a single dose of approximately 700 mg caffeine.

For sleep deprived people, i.e., those who were not able to achieve at least 6 hours of sleep for the preceding day, alertness and stimulation can be imparted through the administration of both lower dosage of caffeine in the formulation as well as the attainment of lower blood plasma levels of caffeine. For these individuals, a blood plasma level of about 4 to 4.5 µg/ml is often sufficient to provide stimulation and alertness. This level can easily be achieved within about 1 to 2 through the administration of a single dose of approximately 300 mg of caffeine. The present invention is further characterized by being able to sustain the minimum level (i.e., the 4.5 or 6.3 value) for a period of between about 2 and 10 hours. Specific formulations and results are presented in the examples.

EXAMPLES

The following examples illustrate preferred aspects of the present invention. In these examples, all parts are by weight and all temperatures are in degrees C unless otherwise indicated. Also, the formulation used in each example had inner and outer layers of matrix with about 85–90% of the active material in the inner layer and the remainder in the outer layer. The formulations contained different amounts of caffeine as recited in the examples.

Example 1

The following clinical drug studies were performed in order to determine an acceptable dosage of caffeine to obtain the desired degree of stimulation and alertness in individuals.

A sustained release formulation was prepared in accordance with the method described above. The microparticles included 700 mg of caffeine per capsule. Size 1 capsules were found to be appropriate for obtaining the desired amount of microparticles therein. One capsule was administered to each of 12 healthy, non-smoking, caffeine-fasting male subjects who were not prone to drinking more than two cups of coffee or tea per day. The subjects' age ranged from 21–33 years and had a mean of 27 years. The blood plasma levels of caffeine in µg/ml were measured prior to administration of the formulation and at each hour thereafter for the next 10 hours followed by a final measurement at 24 hours after administration.

Figure 2:
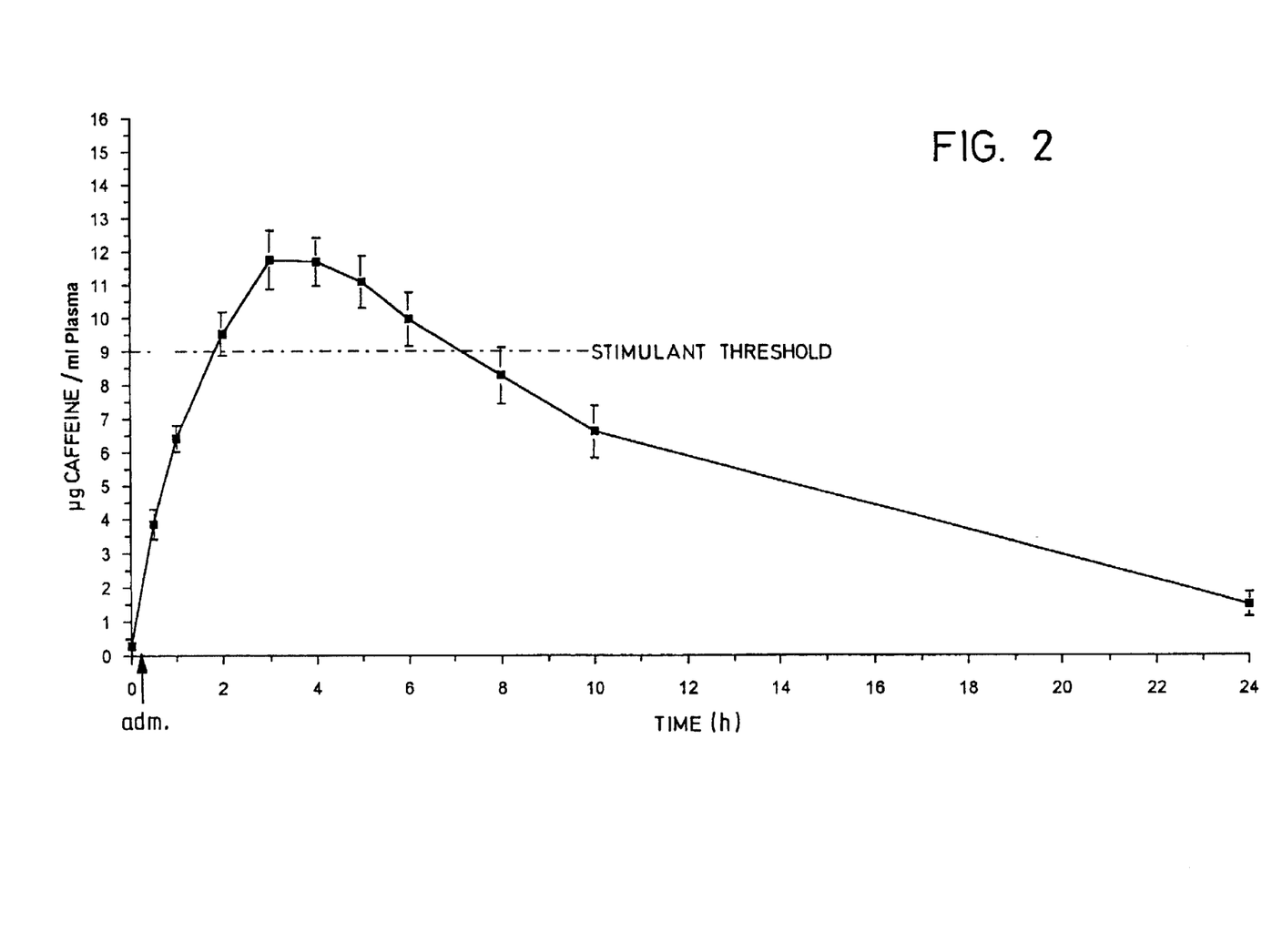
FIG. 2 is a graph which illustrates the blood plasma caffeine levels of healthy, non-smoking male individuals to which have been administered a single dose of 700 mg caffeine in a formulation of the microparticles of FIG. 1.

The mean blood level plasma values are shown in FIG. 2. It was found that the stimulant threshold was approximately 8.5 µg/ml and that the stimulation effect began an average of 1–2 hours after administration and lasted for approximately 5–6 hours. The peak plasma concentration occurred at about 3–4 hours after administration and was on the order of about 10–11 µg/ml of caffeine. The increase in daytime alertness of the individuals was accompanied by a feeling of "energy" and "well being" and there were no significant changes in the sleep patterns of the subjects. Additionally there were no pathological changes in the cardiovascular parameters, although some subjects experienced adverse effects such as headache, nausea, trembling of the extremities and asthenia. A repeated dose study (600 mg caffeine per 24 hours) over a period of 5 days did not reveal any cumulative effects on the various parameters considered.

A similar study was performed in healthy elderly individuals of the ages 65–75 years. The results for these subjects was similar to those obtained in the study of the 21–30 year old individuals.

Example 2

Figure 3:
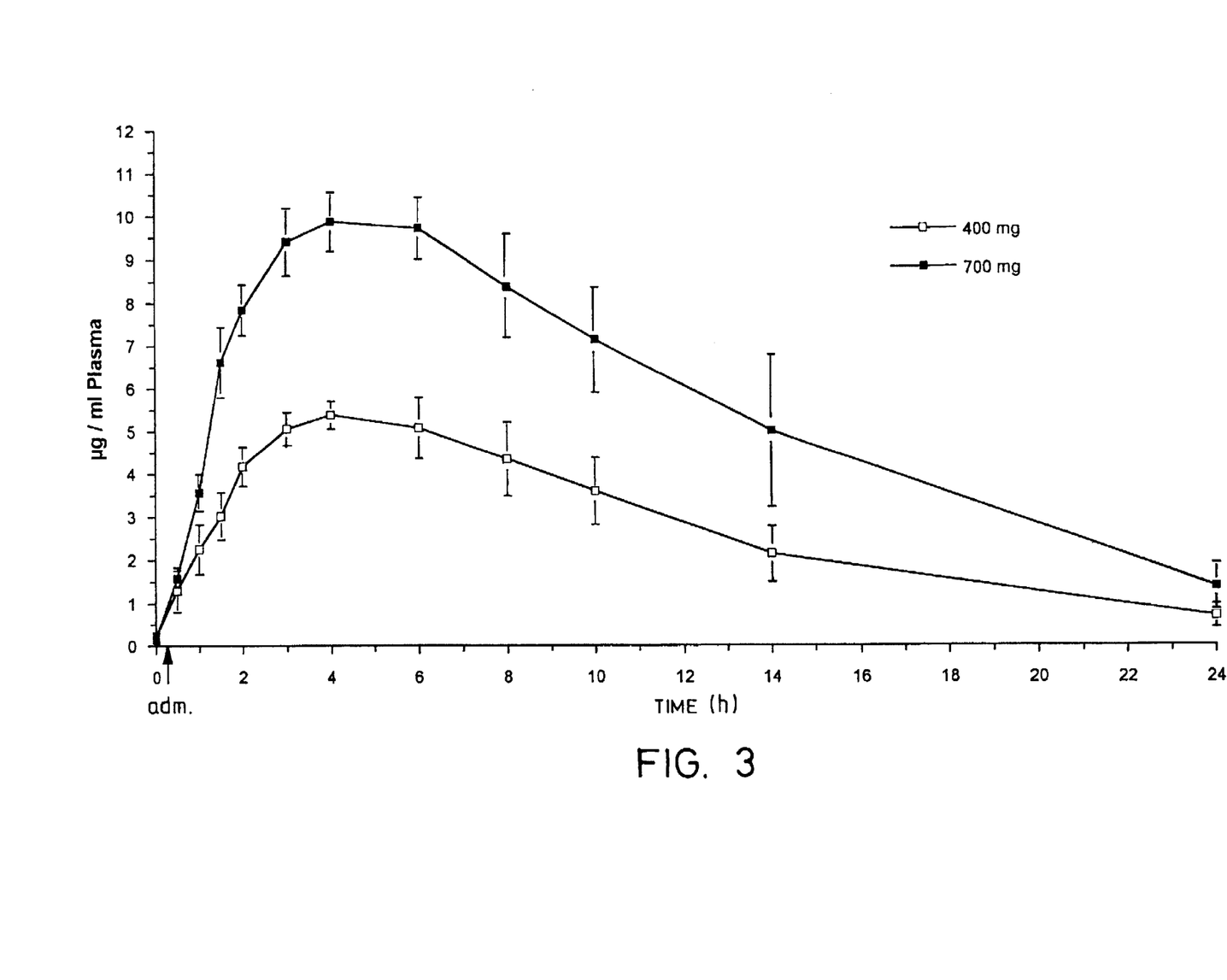
FIG. 3 is a graph which is similar to that of FIG. 2 except that it illustrates the difference between the administration of 400 mg caffeine and 700 mg caffeine.

Two sets of experiments were conducted on two groups of four healthy male subjects aged between 34–44 (with a mean age of 39 years), who normally consume between 3–5 cups of coffee each day. A 400 mg caffeine formulation was administered to one group, while to the second group, a 700 mg formulation was administered. Blood plasma levels were monitored and the results are shown in FIG. 3.

The maximum blood plasma level for the 700 mg formulation occurred at approximately 4.5 hours and achieved a value of 10.14 µg/ml. Similarly, for the 400 mg formulation, the maximum blood plasma level was achieved at approximately the same time but only at a maximum value of 5.51 µg/ml. After 24 hours the blood plasma levels were reduced to 1.38 µg/ml for the 700 mg formulation and 0.69 µg/ml for the 400 mg formulation. For each formulation, the stimulant plasma level was above the stimulation level for approximately 3.5 to 8 hours after administration.

Example 3

A double blind study was conducted to investigate the effects of different dosages of caffeine. The study was performed in two parallel groups of 6 healthy male subjects. Each subject received two different doses of the drug plus one placebo. The duration of this study was for six weeks for each subject, three weeks of inclusion, three treatment periods spaced about one week apart, and one end of the study assessment one week after the last period of administration.

The dosages tested and monitored blood plasma levels were as follows:

| Formulation Dosage (mg) | Maximum caffeine level in blood plasma (µg/ml) |
| --- | --- |
| 600 | 10 |
| 1200 | 20 |
| 1800 | 30 |
| 2400 | 40 |
| 3600 | 60 |
| 4800 | 80 |

This shows that the maximum caffeine concentration is proportional to the dosage. Also, the maximum caffeine level in blood plasma for the slow release caffeine formulations of the invention is approximately 30% lower than that of conventional formulations at the same dosage levels.

Figure 4:
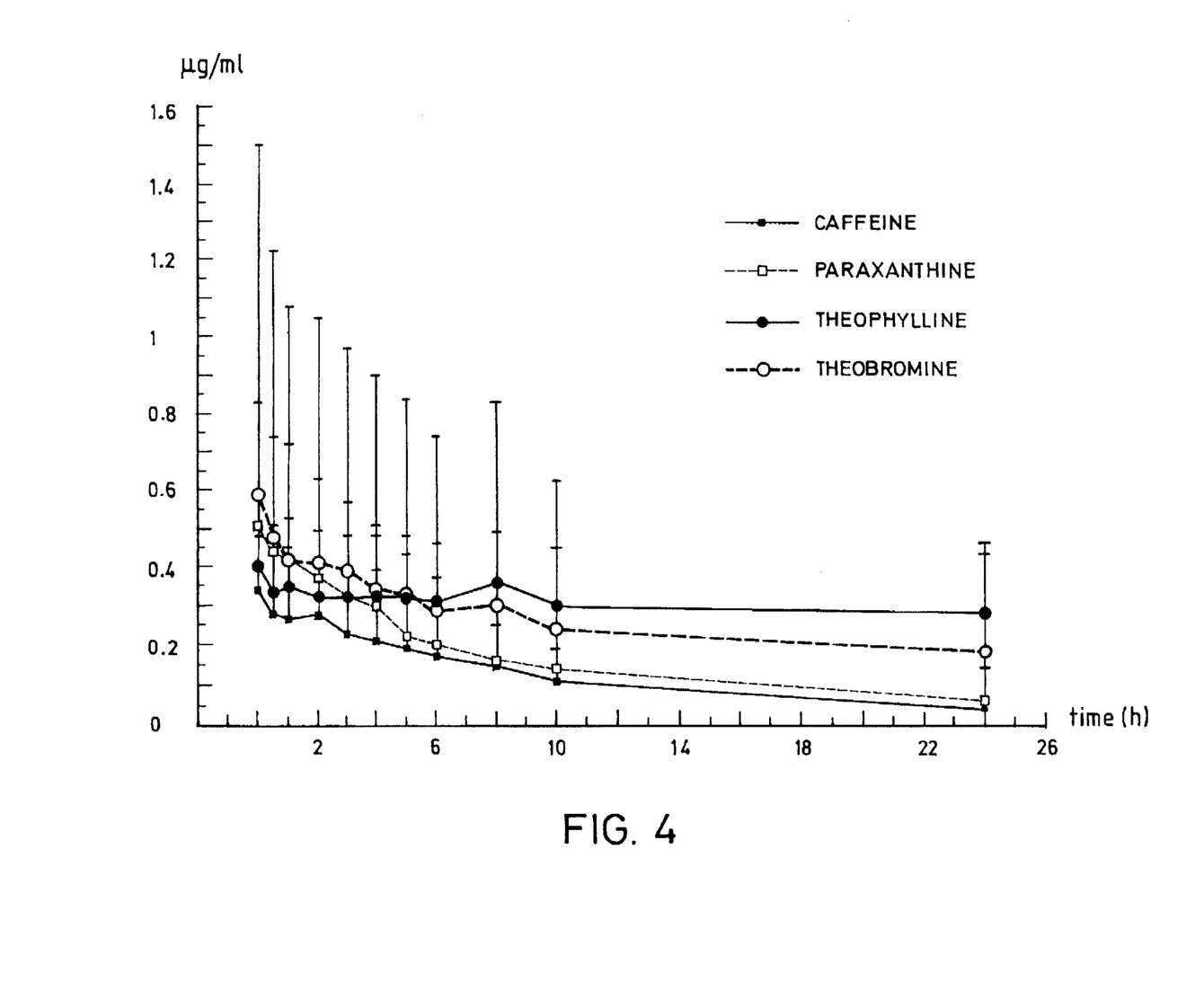
FIGS. 4 and 5 are graphs of the plasma kinetics of caffeine and its metabolites in blood plasma over time after administration.
Figure 5:
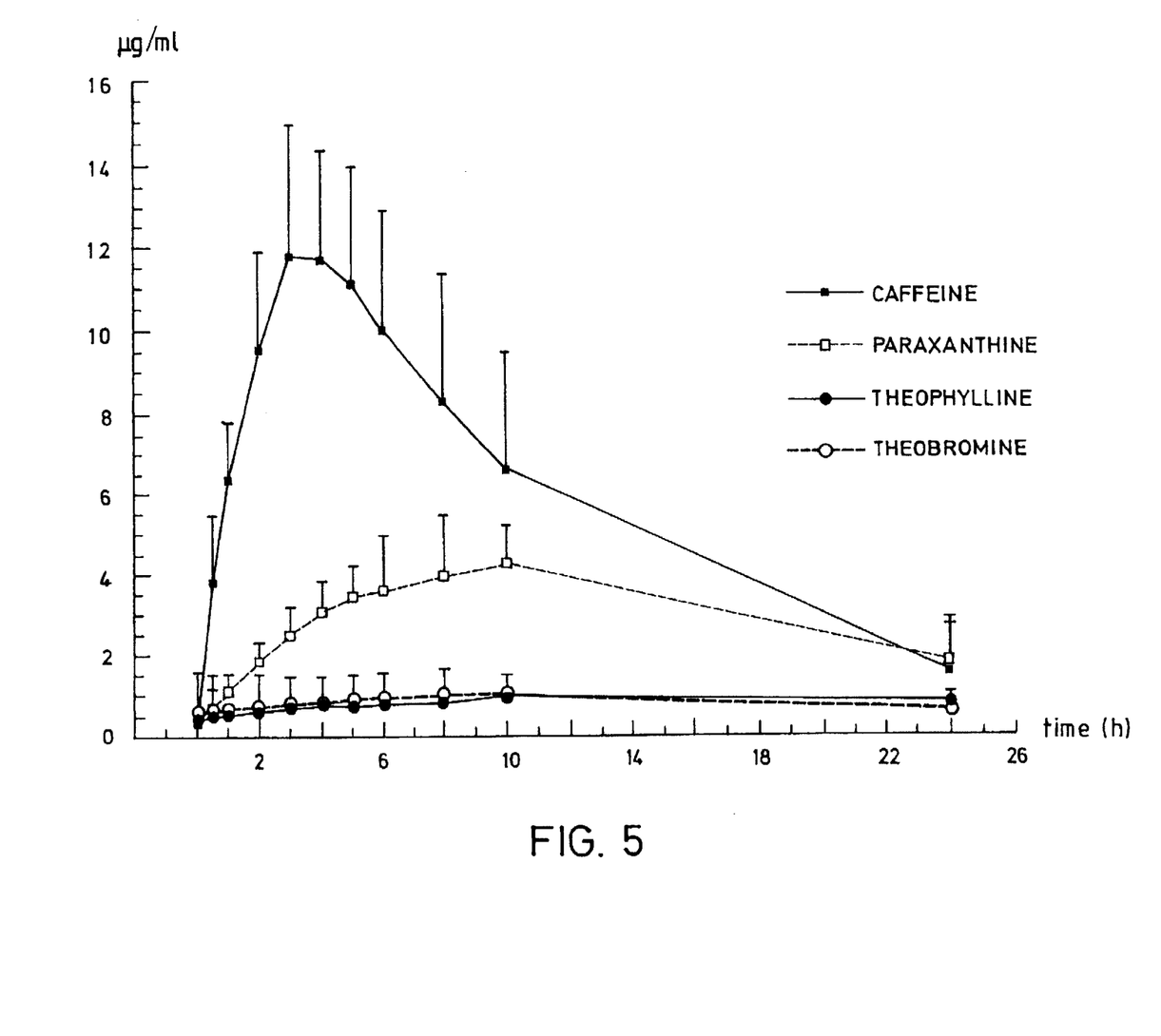

The caffeine, paraxanthine, theophylline and theobromine levels were measured at various times after administration of the placebo, and the results are shown in FIG. 4. The data shows that the levels of each of these components was significantly less than 1 µg/ml. After administration of the caffeine formulation of the invention, the blood plasma level increased significantly and remained above 6 µg/ml for 5–6 hours after administration. This is shown in FIG. 5. Paraxanthine levels also showed an increase, however the theophylline and theobromine levels were about the same as that which was obtained with the placebo.

The plasma concentration for 9 of the 12 subjects fluctuated almost uniformly between 10–15 µg/ml and between 9–10 µg/ml for one individual. The remaining 2 subjects were found to have relatively low plasma caffeine levels ranging between 5–8 µg/ml. From these results, the EEG activity threshold of the slow release caffeine formulation for this study can be considered to be approximately 9 µg/ml of caffeine in blood plasma.

The vital signs of the participants were also measured. Standing heartbeat measurements were found to be slightly elevated although fluctuations were observed after the administration of both the placebo and the caffeine containing formulations of the invention. Also, no abnormalities were observed during the sessions of the study.

Supine blood pressure was measured and the administration of caffeine was found to have a slight effect on arterial pressure with the effect on systolic pressure being especially pronounced. However the elevations were slight on the average and were merely at the limit of biological significance.

Standing blood pressure was also measured in the participants and it was found that the blood pressure was slightly elevated in response to the administration of caffeine. Again this change had no real clinical significance.

Six of the twelve subjects did not experience any side effects. The other six exhibited slight side effects especially at the second testing session where 4 of the 6 reported side effects. These included asthenia, nausea, headache and trembling of upper extremities, and were characterized as being in the range of mild to moderate, but both occurred in the same proportions in the groups that were administered caffeine formulations as well as the placebo. Each subject experienced side effects only once. Aside from the trembling of upper extremities, it is difficult to connect the observed side effects with the ingestion of the slow release caffeine formulation since no significant differences were found between the two groups.

The psychometric scales showed that the ingestion of a single dose of 700 mg of the slow release caffeine formulation increased diurnal alertness but decreased the quality of sleep. The perception of poor sleep quality could have been due to the fact that the subjects had to sleep in a hospital environment. Symbol cross-off and critical flicker fusion tests were unchanged. The effects of the slow release caffeine formulation were visible by hour 2 in 75–80% of the subjects and lasted for 5–6 hours corresponding to blood plasma concentrations of 9–14 µg/ml and at hour 3 in 90% of the subjects and lasted for 5–6 hours corresponding to blood plasma concentrations of above 9 µg/ml. Effects of the slow release caffeine on cerebral electrical activity were found to be very stable with plasma concentrations between 9.6 and 15.9 µg/ml.

After the 10th hour there were no longer any statistically significant changes in the EEG data although two subjects still had plasma caffeine levels of approximately 10 µg/ml. The changes in the energy of cerebral electrical activity confirmed a mild stimulant effect which began 2 hours after the drug was taken and persisted for about 5 hours. The slow release of caffeine from the formulation is accompanied by a decrease in its rate of absorption and a lowering of its plasma peak, thereby decreasing the incidence of side effects. Also the slow release caffeine formulation was as well tolerated as the placebo.

Example 4

A double-blind study of the pharmacokinetics and pharmacodynamic effects on alertness of a slow-release caffeine formulation in four healthy male volunteers requested to fast and given an oral dose of 607 mg caffeine and a placebo, separated by a washout period of one week.

A clinical examination and laboratory tests (blood and urine) were performed on each subject at the time of inclusion. The plasma levels of caffeine and its principal metabolites were measured by a HPLC method over a period of 24 hours post-administration.

Mood was rated (according to the Vas de Norris scale) at 0, 2, 4 and 10 hours, and the quality of sleep and awakening at 24 hours, comparing the night after treatment to the night before. A critical flicker fusion test, a three-symbol cross-off test and an electroencephalographic recording were performed before administration and at 1, 2, 3, 4, 6 and 10 hours afterwards.

The following kinetic parameters were obtained:

| $C_{max}$ µg/ml | $T_{max}$ (h) | AUC (0–12 h) (µg/ml/h) | Vd (l) | Td (Ke) (h) |
|---|---|---|---|---|
| 10.14 | 5.00 | 124.37 | 30.44 | 4.73 |

All the quantitative data were analyzed statistically. The age of the subjects was 25 to 30 years and their body weight 70 to 74 kg. There were no pathological changes in the cardiovascular parameters tested. The psychometric tests were unchanged by the ingestion of the 607 mg slow release caffeine formulation. Although sleep had a tendency to be of slightly poorer quality, daytime alertness increased. The electroencephalogram showed that this formulation causes a moderate and stable stimulation effect characterized by a decrease in slow waves and alpha 1 and 2 activity, and by an increase in activity within the 12–16 Hz band, without any changes in total energy and the position of the maximum peak.

The resultant release for this formulation is considered to be relatively slow, since the maximum blood plasma level of was achieved at about 5–6 hours after administration. The residual plasma level after 24 hours was slightly elevated, and may have contributed to the poorer quality of sleep.

Example 5

In a cross-over protocol, four healthy male subjects were given a single oral dose of 400 and 700 mg of another slow release caffeine formulation before eating a standard breakfast. The two doses were separated by a washout period of two weeks. The caffeine levels post=administration were measured by HPLC in the subjects' plasma and saliva at time 0, 0.5, 1, 1.5, 2, 3, 4, 6, 8, 10, 14 and 24 hours. Heart rate and blood pressure were measured at 0, 1, 3, 4, 8, 14 and 24 hours. At the end of each period, each subject was questioned with regard to mood and sleep quality.

The four male subjects were 34 to 44 years of age and weighed 64 to 80 kg. Two subjects had a slow-acetylator phenotype, while the other two were fast acetylators. The measurement of caffeine levels in the plasma and saliva provided a plasma—saliva conversion factor of 0.71–0.72. The pharmacokinetics results are summarized as follows:

| | $C_{max}$ µg/ml | $T_{max}$ (h) | AUC (0–12 h) (µg/ml/h) | Vd (l) | Td (Ke) (h) |
|---|---|---|---|---|---|
| 400 mg dose | | | | | |
| Plasma | 5.52 | 4.0 | 67.6 | 37.45 | 4.15 |
| Saliva | 3.95 | 5.5 | 49.0 | 66.90 | 4.43 |
| 700 mg dose | | | | | |
| Plasma | 9.40 | 4.0 | 116 | 32.15 | 4.33 |
| Saliva | 7.10 | 5.0 | 82 | 57.75 | 5.43 |

None of the subjects reported any discomfort at the post-administration interviews. In terms of the cardiovascular parameters, there was a slight, insignificant increase in blood pressure, while the heart rate was unchanged.

Example 6

A study was conducted to evaluate the plasma kinetics of caffeine and its metabolites in order to rate the tolerance of the formulation in healthy elderly individuals taking one capsule containing 300 mg of caffeine. The study was performed in two sessions involving 7 subjects each. All of the subjects included in the study following normal clinical examinations and laboratory findings. Each elderly subject took one capsule before eating a standard breakfast. Sitting blood pressure and heart rate were measured at time 0, 2, 4 and 8 hours after treatment, before a saliva specimen was taken, which was done at times 0, 1, 2, 3, 4, 6, 7, 8 and 24 hours post-administration. Caffeine and its metabolites were assayed by a standardized HPLC technique. Each subject answered questions about sleep quality and mood at the end of the study.

The mean age of the subjects was 69 (65–75) years and their mean body weight was 65.6 (40–97) kg. The treatment caused no changes in vital signs, and no adverse effects were observed. The end-of-study interview did not reveal any changes in sleep or awakening. The kinetic parameters obtained were:

| | $C_{max}$ µg/ml | $T_{max}$ (h) | AUC (0–12 h) (µg/ml/h) | Td (Ke) (h) |
|---|---|---|---|---|
| Salivary | 4.69 +/− 0.42 | 5.86 +/− 0.23 | 57.13 +/− 5.18 | 4.32 +/− 0.42 |
| Estimated plasma | 6.14 +/− 0.58 | | 79.35 +/− 7.20 | |

Example 7

A study was performed in 4 male volunteers who took two capsules of 300 mg caffeine every day for 5 days. The study was conducted in the subjects usual environment. They were allowed to drink caffeinated beverages, but not after 14 hours.

Blood pressure and heart rate were checked daily at 0, 4, 8 and 24 hours; salivary levels of caffeine and its metabolites were measured daily at 0, 4, 6, 8, 10 and 24 hours. The subjects rated the quality of their mood, alertness and sleep each day.

The four subjects included in the study ranged in age from 35 to 45 years and weighed 65 to 79 kg. Two subjects had a fast-acetylator phenotype and the other two were slow acetylators. All four were coffee drinkers (3–8 cups per day). Only one was a smoker (30 cigarettes per day).

The elimination kinetics were accelerated in the subject who smoked. No accumulation phenomenon was observed. The peak plasma levels had a tendency to decrease throughout the period of treatment. There was little change in the cardiovascular parameters. No precise trend could be established with regard to the subjective rating of sleep and alertness.

Example 8

A double-blind study of the pharmacokinetic and pharmacodynamic effects on alertness of another slow-release caffeine formulation in twelve healthy male volunteers requested to fast and given an oral dose of 700 mg caffeine and a placebo, separated by a washout period of one week.

A clinical examination and laboratory tests (blood and urine) were performed on each subject at the time of inclusion. The plasma levels of caffeine and its principal metabolites were measured by an HPLC method over a period of 24 hours post-drug.

Mood was rated (according to the Vas de Norris scale) at 0, 2, 4 and 10 hours, and the quality of sleep and awakening at 24 hours, comparing the night after treatment to the night before. A critical flicker fusion test, a three-symbol cross-off test and an electroencephalographic recording were performed before administration and 1, 2, 3, 4, 6 and 10 hours afterward.

Standing and supine systolic blood pressure, diastolic blood pressure and heart rate were recorded on the days of treatment, before and 0.5, 1, 2, 3, 4, 5, 6, 8, 10 and 24 hours after the capsules were taken.

All the quantified data were analyzed statistically. The twelve subjects included in the studies averaged 26.7 years of age, a weight of 70.9 kg and a height of 177.6 cm. The treatment caused significant changes in the following:

The four components of the mood scale (alertness, energy, quick-wittedness, proficiency), all loading onto the factor "alertness," which showed an increase. The three components of sleep (time for and difficulty of falling asleep, and number of episodes of insomnia) varied toward a poorer quality of sleep.

No effects of treatment were observed in either the symbol cross-off test or the critical flicker fusion test.

Conventional electroencephalographic analysis demonstrated that caffeine modified the tracings from the second hour on, but there were no spike, spike-wave or burst-type abnormalities. Spectral analysis revealed a treatment effect that began to be observed an average of two hours after treatment, peaked in about the third hour and disappeared in about the sixth. Overall, this effect was characterized by a decrease in slow theta activity (−18 to −25%) and alpha 1 activity (−17 to −30%), with an equivalent increase in alpha 2 and 3, beta 1 and beta 3. These changes in the EEG tracing manifested an increase in alertness: a moderate, stable stimulant action. Neither the total energy nor the position of the maximum peak were changed. The effect on the EEG could be observed in 75–80% of the subjects by the second hour, corresponding to 9–14 µg/ml, and in 90% of the subjects from 3 hours to 5–6 hours, corresponding to 9.6–15.9 µg/ml.

No major clinical or laboratory anomalies were observed. One case of tremor, nausea, headache and asthenia and two of headache were observed with the caffeine formulation and the placebo, respectively. The electrocardiogram and the blood pressure measurements revealed that the treatment had a positive effect (an increase) on all the parameters except supine heart rate. The observed effects were of low intensity, without any pathological significance.

This formulation is characterized by the following pharmacokinetic parameters:

| $C_{max}$ | $T_{max}$ | AUC (0–24 h) | Vd | $T_e/2$ |
|---|---|---|---|---|
| 12.45 µg/ml | 3.7 h | 145.37 µg/ml/h | 35.5 l | 4.92 h |

The formulation at a dose of 700 mg shows moderate, stable activity of the stimulant type. It increases daytime alertness, with little impact on sleep.

Example 9

A double-blind study of the oral administration of single doses of slow release caffeine formulations according to the invention were studied.

The slow release caffeine formulation was administered at a dose of 600 mg (2 capsules of 300 mg) to 100 healthy volunteers simultaneously, according to a randomized protocol, with 20 subject receiving a placebo. On inclusion, a routine medical examination and an acetylation phenotype determination were performed for each subject. Each was classified according to personal habits such as tobacco consumption and coffee intake. The study was conducted in the subjects' usual environments, but caffeinated beverages were prohibited throughout the test period. Saliva specimens (10 points) were taken during the 24 hours post-drug for HPLC determination of the concentrations of caffeine and its metabolites. A mood rating based on the Vas de Norris scale was performed at times 0, 2, 5 and 10 hours, and the quality of sleep and awakening was evaluated at 24 hours, comparing the night after treatment with the night before.

The 120 male subjects ranged in age from 18 to 26 years, with a mean weight of 70.7 kg. 51% of the subjects were slow acetylators, while the other 49% were fast acetylators. There were no significant differences either between the caffeine and placebo groups or with regard to cardiovascular parameters or personal habits.

The proportions of habitual users of tobacco (53%) and of non-users (42%) were high, while the proportion of occasional smokers was low (5%). The percentage of occasional coffee drinkers (37%) was between that of non-coffee-drinkers (10%) and habitual coffee drinkers (53%). These observations therefore confirm that coffee does not cause dependence.

There was a positive correlation between tobacco consumption and coffee consumption.

Once case of trembling and one of acute asthenia were observed in the 100 subjects treated. One case of nausea was observed in the control group.

The salivary caffeine assays were used to calculate the kinetic parameters of the treated group. Circulating caffeine levels in the 20 subjects taking the placebo were very low, confirming that they had abstained from caffeinated beverages.

Example 10

The purpose of this study was to evaluate, against a placebo, the general clinical, cardiovascular and biological tolerance of a slow release caffeine formulation according to the invention, which was administered in increasing single oral doses of 300, 600, 1200, 2400, 3600 and 4800 mg, in twelve healthy young volunteers. The pharmacokinetic profile of the slow release caffeine formulation and its influence on psychomotor performance was also examined during this study.

The study was designed as a randomized, double-blind, cross-over study versus placebo. There were two parallel groups of six subjects each (3 doses and one placebo per group). Each subject consequently received two increasing doses and a placebo, distributed randomly and separated by a washout period of at least one week.

The 300, 600, 1200 and 1800 mg doses were well tolerated by all subjects. The 2400 mg dose caused nausea and vomiting of low to moderate severity. The 3600 mg dose caused moderate to severe nausea and vomiting. No major cardiovascular reactions were observed. The 4800 mg dose was not administered because of the reactions to the preceding doses. Thus, these results show that formulations which contain 1800 mg dosages or less are preferred.

In terms of tolerance, no severe adverse reactions were observed up to a dose of 1200 mg (18 exposures to drug or placebo). The only adverse reactions were discrete episodes of nausea or palpitations in three subjects during the 1200 mg phase. The clinical tests, and especially the cardiovascular tests, showed nothing of note.

Adverse reactions of the same type but of greater severity were observed during the 2400 mg phase in four subjects. Again, however, no abnormalities were found in these subjects during subsequent clinical examination.

The 3600 mg dose caused adverse reactions whose clinical repercussions were more severe. Two subjects experienced nausea and vomiting that continued on into the evening. The clinical examination revealed nothing of note from a cardiovascular standpoint, however, in one subject, mild pain on epigastric palpitation due to the stress of vomiting was found in addition to asthenia.

To summarize, overall tolerance was found to be completely satisfactory up to a dose of 1200 mg, while above 2400 mg, certain adverse reactions began to increase in severity. The 1800 mg dose was found to be preferred, since it was well tolerated, without any significant adverse effects, in most of the test subjects.

The above description is merely illustrative of the most preferred embodiments of the invention, and other parameters and modifications may be used without departing from the inventive concept disclosed herein. Accordingly, all modifications which are within the true spirit and scope of the present invention and which are within the level of one skilled in the art who has this disclosure before him are intended to be covered by the claims appended hereto.

What is claimed is:

1. A sustained release stimulant composition of microparticles comprising:
   a stimulant of xanthine or a xanthine derivative; and
   substantially spherical solid cores of pharmaceutically acceptable organic material, having:
   a) a first layer substantially surrounding the core which comprises a biodegradable matrix of a water soluble binding agent, a water insoluble release retarding agent, and between about 55–95% by weight of the total amount of stimulant present in the particle, wherein:
      i) the binding agent binds the stimulant to the microparticle;
      ii) the release retarding agent retards the release of the stimulant from the matrix; and
      iii) the stimulant is uniformly distributed in the matrix;
   b) a second layer substantially surrounding the first layer which comprises a water insoluble material for further delaying the release of the stimulant from the first layer; and
   c) a third layer substantially surrounding the second layer which comprises a biodegradable matrix of a water soluble binding agent, a water insoluble release retarding agent and between about 5–45% by weight of the total amount of the stimulant present in the particle, wherein:
      i) the binding agent binds the stimulant to the microparticle;
      ii) the release retarding agent retards the release of the stimulant from the matrix; and
      iii) the stimulant is uniformly distributed in the matrix,
   and further wherein:
      A) at least about 20–50% by weight of the total amount of the stimulant present in the composition is capable of being released within about 2 hours following oral administration; and
      B) the balance of the stimulant is capable of being released within about 8–10 hours following oral administration.

2. The composition according to claim 1, wherein the amount of stimulant present in the first layer is at least about 80% by weight of the total amount present in each microparticle and the amount of stimulant in the third layer is no more than about 20% by weight of the total amount present in each microparticle.

3. The composition of claim 1, wherein the core comprises a polysaccharide, sugar or a sugar derivative, and optionally a diluent.

4. The composition of claim 2, wherein the core comprises sucrose and the diluent is a starch which is in intimate association with the sucrose.

5. The composition according to claim 1, wherein the water soluble binding agent is a synthetic polymer and the water insoluble retarding agent is a shellac.

6. The composition according to claim 1, wherein the second layer comprises a shellac with a given thickness to further delay the release of the stimulant from the matrix.

7. The composition of claim 5, wherein the second layer further comprises talc in an amount effective to help prevent the coated microparticles from sticking together.

8. A composition for the controlled release of a stimulant which comprises a capsule containing the composition according to claim 1.

9. The composition of claim 7, wherein the stimulant is caffeine and the microparticles have a final diameter of between about 0.7 and 1.2 mm.

10. The composition of claim 8, wherein the amount of caffeine in each capsule is between about 100 and 700 mg.

11. The composition of claim 8, wherein the amount of caffeine in each capsule is between about 200 and 400 mg.

12. The composition according to claim 1 or 7, in which at least about 35% to 50% of the total weight of the stimulant present in the composition is capable of being released within about two hours after administration and at least about 70% of the total weight of the stimulant present in the composition is capable of being released within about five hours after administration.

13. The composition of claim 1 or 7, in which at least about 20% to 35% of the total weight of the stimulant present in the composition is capable of being released within about one hour after administration and at least about 90% of the total weight of the stimulant present in the composition is capable of being released within about six hours after administration.

14. A sustained release stimulant composition of microparticles consisting essentially of:
   a stimulant of xanthine or a xanthine derivative; and
   substantially spherical solid cores of pharmaceutically acceptable organic material, having:
   a) a first layer substantially surrounding the core which consists essentially of a biodegradable matrix of a water soluble binding agent, a water insoluble release retarding agent, and between about 55–95% by weight of the total amount of stimulant present in the particle, wherein:
      i) the binding agent binds the stimulant to the microparticle;
      ii) the release retarding agent retards the release of the stimulant from the matrix; and
      iii) the stimulant is uniformly distributed in the matrix;
   b) a second layer substantially surrounding the first layer which consists essentially of a water insoluble material for further delaying the release of the stimulant from the first layer; and
   c) a third layer substantially surrounding the second layer which consists essentially of a biodegradable matrix of a water soluble binding agent, a water insoluble release retarding agent and between about 5–45% by weight of the total amount of the stimulant present in the particle, wherein:
i) the binding agent binds the stimulant to the microparticle;
ii) the release retarding agent retards the release of the stimulant from the matrix; and
iii) the stimulant is uniformly distributed in the matrix, and further wherein:
A) at least about 20–50% by weight of the total amount of the stimulant present in the composition is capable of being released within about 2 hours following oral administration; and
B) the balance of the stimulant is capable of being released within about 8–10 hours following oral administration.

* * * * *